United States Patent [19]

Robin et al.

[11] Patent Number: 4,806,544

[45] Date of Patent: Feb. 21, 1989

[54] ASYMMETRICAL ESTER DERIVATIVES OF 1,4-DIHYDROPHYRIDINE-3,5-DICARBOXYLIC ACID

[75] Inventors: Jacques Robin; Didier Pruneau, both of Dijon; François Bellamy, Saulon La Rue, all of France

[73] Assignee: Fournier Innovation et Synergie, Paris, France

[21] Appl. No.: 27,262

[22] Filed: Mar. 18, 1987

[30] Foreign Application Priority Data

Apr. 2, 1986 [FR] France ................. 86 04685

[51] Int. Cl.[4] ................. A61K 31/445; C07D 491/20
[52] U.S. Cl. ....................... 514/278; 546/19
[58] Field of Search ................. 514/278; 546/19

[56] References Cited

U.S. PATENT DOCUMENTS

| 4,250,312 | 2/1981 | Nakahara et al. | 546/19 |
| 4,250,313 | 2/1981 | Nakahara et al. | 546/19 |
| 4,710,505 | 12/1987 | Robin et al. | 514/278 |

FOREIGN PATENT DOCUMENTS 088903  9/1983  European Pat. Off. ............ 546/194

OTHER PUBLICATIONS

Chemical Abstracts, vol. 82, No. 21, May 26, 1975, p. 627, 28-Heterocycles, No. 140108j.

*Primary Examiner*—Robert T. Bond
*Attorney, Agent, or Firm*—Holman & Stern

[57] ABSTRACT

The present invention relates to novel asymmetrical esters derived from 1,4-dihydrophyridine-3,5-dicarboxylic acid, of the formula:

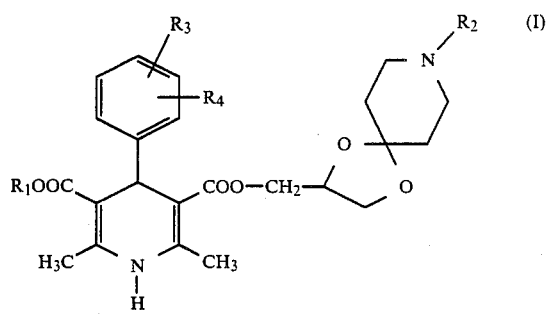

in which: $R_1$ represents a $C_1$–$C_4$ alkyl group, $R_2$ represents a $C_1$–$C_4$ alkyl group, a benzyl group, a benzoyl group or a phenyl group optionally substituted by one or more $C_1$–$C_4$ alkoxy, $C_1$–$C_4$ alkyl, cyano, nitro, hydroxyl or trifluoromethyl groups or by one or more halogen atoms, and $R_3$ and $R_4$, which are identical or different, each represent the hydrogen atom, a nitro group or a chlorine atom, their optical isomers and diastereoisomers and also the corresponding addition salts.

These novel esters are useful in therapy, especially as antihypertensives.

10 Claims, No Drawings

ASYMMETRICAL ESTER DERIVATIVES OF 1,4-DIHYDROPHYRIDINE-3,5-DICARBOXYLIC ACID

FIELD OF THE INVENTION

The present invention relates to novel derivatives of 1,4-dihydropyridine-3,5-dicarboxylic acid. It also relates to the methods for their preparation and to their application in therapy.

PRIOR ART

French patent application No. 85-02412, filed in the name of the Applicant Company, describes asymmetrical heterocyclic esters of 1,4-dihydropyridine-3,5-dicarboxylic acids which correspond to the formula:

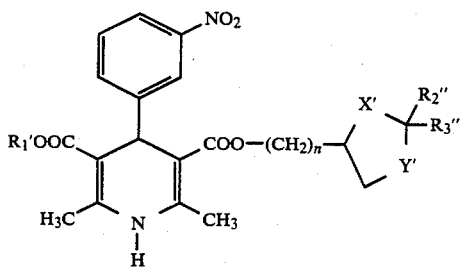
(I$_o$)

in which, in particular, $R'_1$ is $C_1$-$C_4$ alkyl, n is the integer 1 or 2, $X'$ and $Y'$ each represent O or S, at least one of the symbols $X'$ and $Y'$ being different from S, and $R''_2$ and $R''_3$ each represent the hydrogen atom, the methyl group or phenyl or halogenophenyl groups or together form a spirocycloaliphatic group.

These products are indicated as vasodilators and differ from the known products of the prior art especially in their antihypertensive effects and their effects on the cardiac, femoral and coronary outputs.

OBJECT OF THE INVENTION

The Applicant Company has attempted to optimize the pharmacological properties of these products and has now just found novel 1,4-dihydropyridine-3,5-dicarboxylic acid derivatives which differ from the products of the above-mentioned Application especially in their structure and their activity when administered orally.

DETAILED DISCLOSURE OF THE INVENTION

The novel derivatives according to the invention are selected from the group comprising:
(i) the esters corresponding to the general formula:

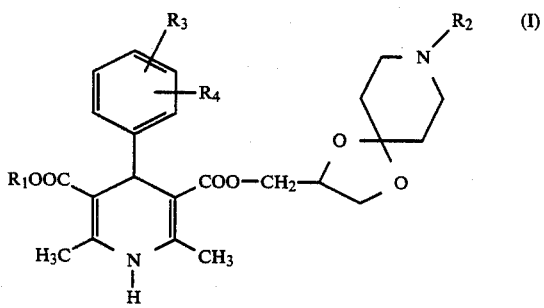
(I)

in which: $R_1$ represents a $C_1$ to $C_4$ alkyl group, $R_2$ represents a $C_1$-$C_4$ alkyl group, a benzyl group, a benzoyl group or a phenyl group optionally substituted by one or more $C_1$-$C_4$ alkoxy, $C_1$-$C_4$ alkyl, cyano, nitro, hydroxyl or trifluoromethyl groups or by one or more halogen atoms, and $R_3$ and $R_4$, which are identical or different, each represent a hydrogen atom, a nitro group or a chlorine atom;
(ii) their optical isomers and diastereoisomers; and
(iii) the corresponding addition salts.

The groups $CH_3$, $CH_2CH_3$, $CH(CH_3)_2$, $C(CH_3)_3$, $OCH_3$, $OCH_2CH_3$, $OCH(CH_3)_2$ and $OC(CH_3)_3$ may be mentioned in particular among the alkyl and alkoxy groups which are covered by the definition of the groups $R_1$ and $R_2$ referred to above.

The fluorine, chlorine and bromine atoms may be mentioned among the halogen atoms which are esuitable according to the invention, the preferred halogen atom being the chlorine atom.

The preferred groups which $R_3$ and $R_4$ form with the phenyl nucleus to which they are bonded are the 3-nitrophenyl groups and the 2,3-dichlorophenyl group.

The compounds of the formula (I) according to the invention can be prepared by two methods:

Method A consists in reacting a benzylideneacetoacetate of the formula:

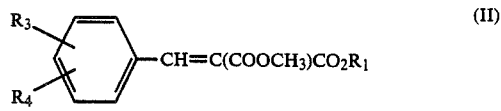
(II)

in which $R_1$, $R_3$ and $R_4$ are defined as indicated above, with an aminocrotonate of the formula:

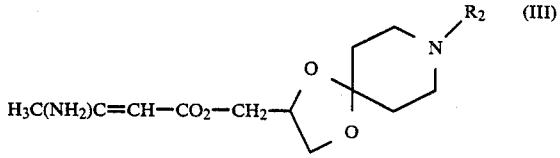
(III)

in which $R_2$ is defined as indicated above, in accordance with the so-called Hantzsch reaction.

Advantageously, about 1 mol of II is reacted with about 1 mol of III in a polar organic solvent (especially a $C_1$-$C_4$ alkanol such as methanol, ethanol, isopropanol, n-butanol or t-butanol), for 1 to 24 h, at a temperature between room temperature (15°-20° C.) and the reflux temperature of the reaction medium.

The compounds of the formula II are known substances which can be prepared in accordance with the so-called Knoevenagel reaction, cf. the review article by G. Jones, Organic Reactions, 15, 204 (1975).

The compounds of the formula III are novel products, the recommended method for their preparation being as follows:
(1) reaction of an alcohol of the formula:

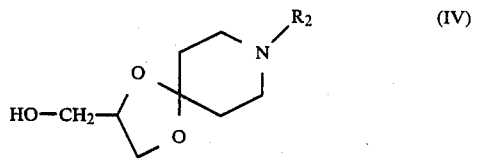
(IV)

in which $R_2$ is defined as indicated above, with acetylated Meldrum's acid of the formula:

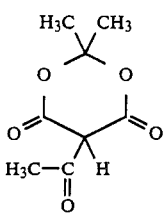

in an aromatic solvent (especially benzene, toluene or xylenes), at a temperature between room temperature (15°-20° C.) and the reflux temperature of the reaction medium, for 0.2 to 4 h, to give a novel ketoester of the formula:

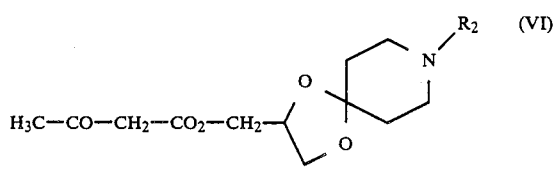

in which $R_2$ is defined as indicated above, and (2) treatment of the resulting derivative of the formula VI with $NH_3$ in a chlorinated solvent (especially $CH_2Cl_2$ or $CHCl_3$) for 1 to 24 h.

The compounds of the formulae III and VI can be used without prior purification. Advantageously, they are used after they have been purified either by distillation (or recrystallization) or by flash chromatography (column chromatography under pressure) in accordance with the technique described by W. C. Still et al., J. Org. Chem., 43 (no. 14), 2923 (1978).

The ketoesters of the formula VI and the aminocrotonates of the formula III, which were prepared as indicated above and are involved in the synthesis of the compounds according to the invention, have been collated in the following Tables I and II respectively, without implying a limitation.

TABLE I $H_3C-CO-CH_2-CO_2-CH_2\text{-spiro-piperidine-}R_2$

| $R_2$ | Reaction time (hours) | Solvent | Method of purification | Yield (%) | NMR spectrum (b) |
|---|---|---|---|---|---|
| —$CH_3$ | 1 | toluene | flash chromatography toluene/isopropanol/ triethylamine (95:5:5 v/v/v) | 44 | 1.6–1.85 (4H, m); 2.27 (3H, s); 2.29 (3H, s); 2.3–2.6 (4H, m); 3.5 (2H, s); 3.6–4.5 (5H, m) |
| —$CH_2$—phenyl | 2 | toluene | flash chromatography toluene/ethyl acetate (6:4 v/v) | 71 | 1.6–1.9 (4H, m); 2.25 (3H, s); 2.3–2.7 (4H, s); 3.5 (2H, s); 3.55 (2H, s); 3.6–4.4 (5H, m); 7.2–7.4 (5H, m) (60 MHz) |
| —C$_6$H$_4$—F | 3 | toluene | (a) | 100 | 1.7–2 (4H, m); 2.27 (3H, s); 3.1–3.3 (4H, m); 3.5 (2H, s); 3.6–4.5 (5H, m); 6.8–7 (4H, m) |
| —C$_6$H$_4$—OCH$_3$ | 3 | toluene | (a) | 100 | 1.7–2 (4H, m); 2.27 (3H, s); 3.0–3.35 (4H, m); 3.5 (2H, s); 3.76 (3H, s); 4.0–4.5 (5H, m); 6.7–6 (4H, m) |
| —C$_6$H$_3$(OCH$_3$)$_2$ | 3 | toluene | (a) | 94 | 1.75–2 (4H, m); 2.27 (3H, s); 3.1–3.3 (4H, m); 3.5 (2H, s); 3.83 (3H, s); 3.86 (3H, s); 3.7–4.5 (5H, m); 6.4–6.9 (3H, m) |
| —C$_6$H$_4$—CN | 2 | toluene | flash chromatography toluene/ethyl acetate (9:1 v/v) | 70 | 1.8–2.1 (4H, m); 2.3 (3H, s); 3.1–3.4 (4H, m); 3.5 (2H, s); 3.7–4.6 (5H, m); 6.8–7.6 (4H, m) (60 MHz) |

TABLE I-continued

H₃C—CO—CH₂—CO₂—CH₂—[spiro dioxolane-piperidine with N-R₂]

| R₂ | Reaction time (hours) | Solvent | Method of purification | Yield (%) | NMR spectrum (b) |
|---|---|---|---|---|---|
| —C₆H₄—NO₂ (para) | 0.3 | benzene | chromatography hexane/acetone (7:3 v/v) | 68 | 1.6–1.95 (4H, m); 2.27 (3H, s); 3.4–3.7 (m) and 3.5 (s) (6H); 3.75–4.5 (5H, m); 6.8 (2H, d); 8.1 (2H, d) |
| —C₆H₄—CN (para) | 3 | toluene | (a) | 100 | 1.6–1.9 (4H, m); 2.25 (3H, s); 3.3–3.6 (m) and 3.5 (s) (7H); 3.7–4.6 (5H, m); 6.85 (2H, d); 7.45 (2H, d) (60 MHz) |
| —C₆H₄—CF₃ (para) | 2 | toluene | (a) | 100 | 1.5–2 (4H, m); 2.27 (3H, s); 3.3–4.6 (m) and 3.5 (s) (6H); 4–4.5 (5H, m); 6.8–6.95 (2H, d); 7.35–7.5 (2H, d) |
| —C(=O)—C₆H₅ | 1 | toluene | flash chromatography hexane/acetone (7:3 v/v) | 94 | 1.6–1.9 (4H, m); 2.26 (3H, s); 3.4–4.4 (m) and 3.5 (s) (11H); 7.2–7.6 (5H, m) |
| —C₆H₄—CF₃ (meta) | 2 | toluene | (a) | 90 | 1.7–2.05 (4H, m); 2.28 (3H, s); 3.3–3.45 (4H, m); 3.5 (1.8H, s); 3.7–4.5 (5H, m); 5.04 (0.1 H, s); 6.9–7.5 (4H, m); 11.9 (0.1 H, s) |

Notes:
(a) without purification
(b) spectrum run at 80 MHz unless indicated otherwise, in CDCl₃, relative to TMS

TABLE II

H₃C(NH₂)C=CH—CO₂—CH₂—[spiro dioxolane-piperidine with N-R₂]

| R₂ | Reaction time (hours) | Solvent | Method of purification | Yield (%) | NMR spectrum |
|---|---|---|---|---|---|
| —CH₃ | 5 | methanol | flash chromatography toluene/isopropanol/ triethylamine (95:5:5 v/v/v) | 44 | 1.6–1.95 (m) and 1.9 (s) (7H); 2.3 (3H, s); 2.3–2.48 (4H, m); 3.6–4.4 (5H, m); 4.55 (1H, s) |
| —CH₂—C₆H₅ | 5 | methylene chloride | (a) | 98 | 1.65–2 (m) + 1.9 (s) (7H); 2.4–2.75 (4H, m); 3.55 (2H, s); 3.6–4.5 (5H, m); 4.6 (1H, s); 7.25–7.4 (5H, m) |
| —C₆H₄—F (para) | 4 | chloroform | (a) | 100 | |
| —C₆H₄—OCH₃ (para) | 3 | chloroform | (a) | 100 | 1.7–2 (m) + 1.9 (s) (7H); 3.1–3.4 (4H, m); 3.76 (3H, s); 3.9–4.5 (5H, m); 4.54 (1H, s); 6.7–7 (4H, m) |

TABLE II-continued

H₃C(NH₂)C=CH—CO₂—CH₂— [piperidine ketal structure with R₂ on N]

| R₂ | Reaction time (hours) | Solvent | Method of purification | Yield (%) | NMR spectrum |
|---|---|---|---|---|---|
| 2,3-dimethoxyphenyl (—C₆H₃(OCH₃)₂) | 4 | chloroform | (a) | 100 | 1.75–2 (m) + 1.9 (s) (7H); 3–3.3 (4H, m); 3.82 (3H, s); 3.86 (3H, s); 3.6–4.5 (5H, m); 4.55 (1H, s); 6.4–6.8 (3H, m) |
| 2-cyanophenyl | 12 | methylene chloride | (a) | 100 | 1.8–2.1 (m) + 1.9 (s) (7H); 3.1–3.4 (4H, m); 3.7–4.45 (5H, m); 4.55 (5H, m); 4.55 (1H, s); 6.8–7.6 (4H, m) (60 MHz) |
| 4-nitrophenyl | 2 | methylene chloride | (a) (b) | 97 | 1.6–1.95 (m) + 1.9 (s) (7H); 3.4–3.7 (m, 4H); 3.8–4.55 (m, 5H); 4.55 (1H, s); 6.8 (2H, d); 8.1 (2H, d) |
| 4-cyanophenyl | 24 | methylene chloride | (a) (c) | 77 | 1.6–1.9 (m) + 1.9 (s) (7H); 3.3–3.6 (4H, m); 3.7–4.5 (5H, m); 4.55 (1H, s); 6.85 (2H, d); 7.45 (2H, d) (60 MHz) |
| 4-(trifluoromethyl)phenyl | 11 | chloroform | (a) | 100 | 1.7–2 (m) + 1.9 (s) (7H); 3.25–3.6 (4H, m); 3.7–4.4 (5H, m); 4.56 (1H, s); 6.8–6.95 (2H, d); 7.35–7.5 (2H, d) |
| benzoyl (PhC(O)—) | 12 | methylene chloride | (a) | 100 (crude) | 1.55–1.95 (m) + 1.9 (s) (7H); 3.4–4.4 (9H, m); 4.5 (1H, s); 7.2–7.6 (5H, m) |
| 3-(trifluoromethyl)phenyl | 12 | chloroform | (a) | 100 (crude) | 1.7–2 (m) + 1.9 (s) (7H); 3.2–3.5 (4H, m); 3.7–4.5 (6H, m); 4.56 (1H, s); 6.9–7.5 (4H, m) |

Notes:
(a) without purification
(b) melting point: 176° C.
(c) melting point: 170–175° C.
(d) spectrum run at 80 MHz unless indicated otherwise, in CDCl₃, relative to TMS

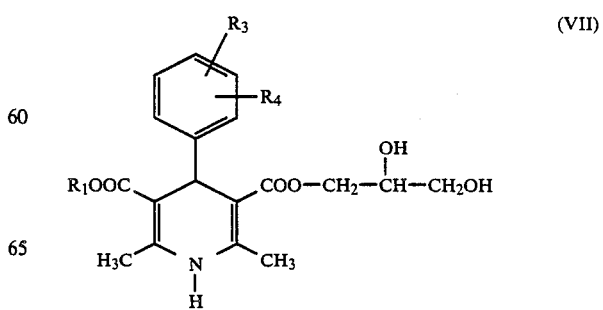

(VII)

Method B consists of a ketalization in which a protected or unprotected diol of the formula:

in which $R_1$, $R_3$ and $R_4$ are defined as indicated above, is reacted with a piperidinone of the formula:

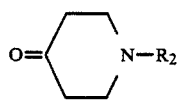

(VIII)

in which $R_2$ is defined as indicated above.

The diol of the formula VII can be used in protected form, for example in the form of a substituted or unsubstituted methyl or ethyl ether, a silylated ether, an ester, a carbonate, an acetal, for example the acetanilide, a cyclopentylidene, cyclohexylidene or benzylidene or a cyclic orthoester.

Advantageously, about 1 mol of VII is reacted with about 1 mol of VIII in a polar organic solvent, for example a $C_1$-$C_4$ alcohol, an aromatic solvent such as benzene, xylenes or toluene, or mixtures thereof, in the presence of a mineral acid, for example sulfuric or hydrochloric acid, or an organic acid, for example paratoluenesulfonic or benzenesulfonic acid, at a temperature between room temperature and the reflux temperature of the reaction medium, for 1 to 12 hours.

The compound of the formula VII can be prepared by a method known per se, especially for opening the dioxolanyl ring of a compound of the formula:

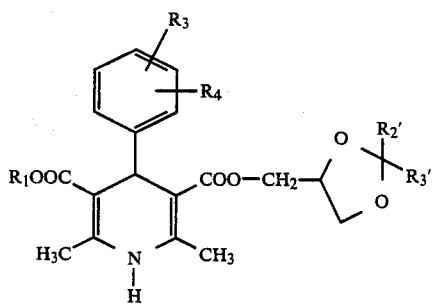

(IX)

in which $R_1$, $R_3$ and $R_4$ are defined as indicated above and $R'_2$ and $R'_3$ each represent H or a $C_1$-$C_4$ alkyl group, in an acid medium.

A number of compounds of the formula I according to the invention have been collated in the following Table III, without implying a limitation.

TABLE III

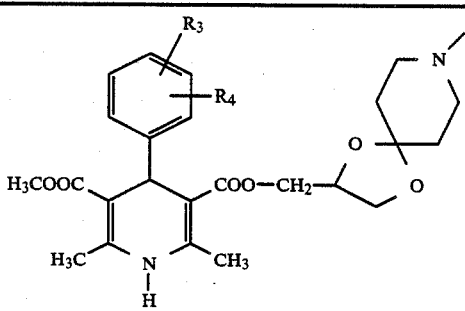

| Example | $R_2$ | $R_3$ | $R_4$ | M.p. (°C.) |
|---|---|---|---|---|
| 1 | 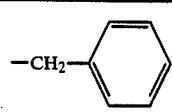 -CH₂-⌬ | 3-NO₂ | H | 87 |

TABLE III-continued

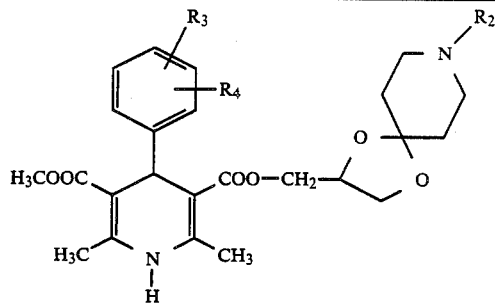

| Example | $R_2$ | $R_3$ | $R_4$ | M.p. (°C.) |
|---|---|---|---|---|
| 2 | phenyl | 3-NO₂ | H | 89 |
| 3 | —CH₃ | 3-NO₂ | H | 62 to 76 (a) |
| 4 | 4-OCH₃-phenyl | 3-NO₂ | H | 65 to 85 (a) |
| 5 | 3,4-di-OCH₃-phenyl | 3-NO₂ | H | 65 to 85 (a) |
| 6 | 4-F-phenyl | 3-NO₂ | H | 70 to 95 (a) |
| 7 | —C(O)-phenyl (benzoyl) | 3-NO₂ | H | 95 to 115 (a) |
| 6 | 2-CN-phenyl | 3-NO₂ | H | 70 to 93 (a) |
| 9 | 4-NO₂-phenyl | 3-NO₂ | H | 85 to 108 (a) |
| 10 | 4-CN-phenyl | 3-NO₂ | H | 115 |
| 11 | 4-Cl-phenyl | 3-NO₂ | H | 75 to 80 (a) |
| 12 | 4-CF₃-phenyl | 3-NO₂ | H | 65 to 95 (a) |

TABLE III-continued

[Structure shown with R3, R4 on phenyl ring; H3COOC and COO—CH2— groups on dihydropyridine with H3C, CH3, and NH; piperidine N—R2 with dioxolane linker]

| Example | R2 | R3 | R4 | M.p. (°C.) |
|---|---|---|---|---|
| 13 | 3-CF3-phenyl | 3-NO2 | H | 62 to 110 (a) |
| 14 | 4-OH-phenyl | 3-NO2 | H | 75 to 85 (a) |
| 15 | 4-CH3-phenyl | 3-NO2 | H | 102 to 114 (a) |
| 16 | 3,4-diCl-phenyl | 3-NO2 | H | 80 to 95 (a) |
| 21 | 4-Cl-phenyl | 2-Cl | 3-Cl | 100 |

Notes:
(a) These products do not have a sharp melting point and melt over the range indicated.
(b) foam The enantiomers and diastereoisomers can be separated from the corresponding racemates by a method known per se, especially by fractional crystallization, by resolution or by some other method.

The enantiomers according to the invention can also be prepared by a method wherein:
(1) a dihydropyridine of the formula:

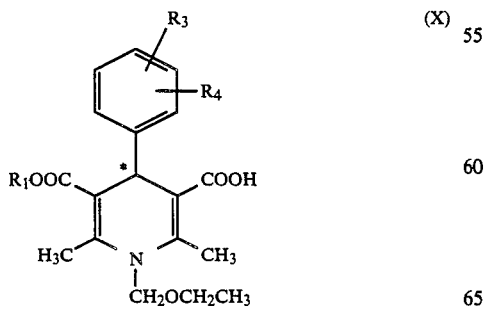
(X)

in which $R_1$, $R_3$ and $R_4$ are defined as above and the carbon marked * has the R configuration or the S configuration, is reacted with carbonyldiimidazole, and,
(2) without isolation of the intermediate derivative formed, the reaction medium is reacted with an alcohol of the formula:

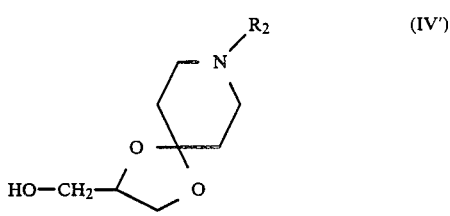
(IV')

in which $R_2$ is defined as above and the carbon marked * has the R configuration or the S configuration, to give a compound of the formula:

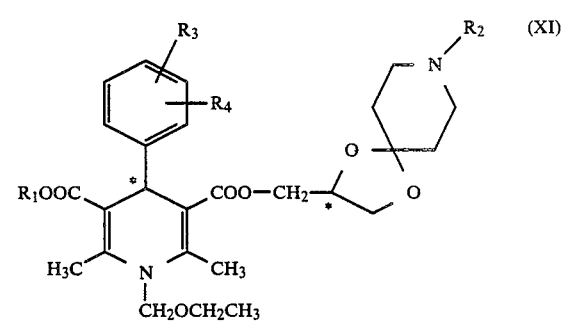
(XI)

in which $R_1$, $R_2$, $R_3$ and $R_4$ are defined as above and the carbons marked * have the R configuration or the S configuration, and
(3) the compound of the formula XI is treated in an acid medium to give a compound of the formula:

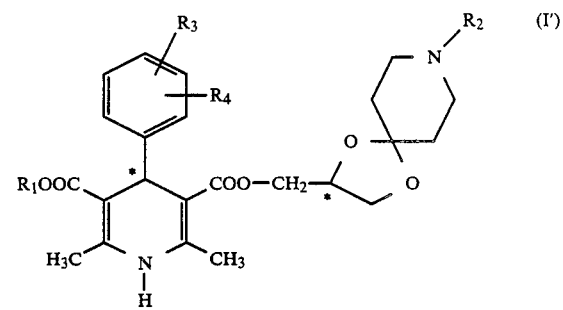
(I')

in which $R_1$, $R_2$, $R_3$ and $R_4$ are defined as above and the carbons marked * have the R configuration or the S configuration.

Advantageously, about 1 mol of X is reacted with about 1 mol of carbonyldiimidazole in an inert organic solvent (especially dimethylformamide, dimethylacetamide or dimethyl sulfoxide), for 0.5 to 4 h, at a temperature between room temperature (15°–20° C.) and about 80° C., about 1 mol of IV' and about 1 mol of a strong organic base (especially 1,8-diazabicyclo[5.4.0]undec-7-ene, 1,5-diazabicyclo[4.3.0]non-5-ene or 4-dimethylaminopyridine) are then added and the reaction medium is heated at a temperature of between about 40° C. and about 150° C. for 1 to 10 h. The compound of the formula XI is isolated in the conventional way and treated in a strong acid medium (especially N hydrochloric acid), in an organic solvent (especially a ketone), to give an optically active compound of the formula I'.

The compounds of the formula I can be converted to salts by the conventional methods known to those skilled in the art. Preference will be given in particular to the addition salts obtained by reaction with biologically acceptable strong acids, for example hydrochloric, hydrobromic, methanesulfonic, nitric or sulfuric acid.

According to the invention, a therapeutic composition is recommended which contains, in association with a physiologically acceptable excipient, at least one compound selected from the group comprising the derivatives of the formula I above, their enantiomers and diastereoisomers and their addition salts.

Of course, in a composition of this type, the active principle is present in a pharmaceutically effective amount.

According to the invention, it is also recommended to use a substance selected from the group comprising (i) the derivatives of the formula I, (ii) their enantiomers and diastereoisomers, and (iii) their nontoxic addition salts, in order to obtain an antihypertensive drug to be used in human therapy for the treatment of hypertension and cardiac insufficiencies.

Further advantages and characteristics of the invention will be understood more clearly from the following description of preparative examples and results of pharmacological tests. These data as a whole do not imply a limitation but are given by way of illustration. In the said examples, the R and S configurations are denoted in accordance with the nomenclature rules in Chemical Abstracts.

PREPARATION I

Preparation of (8-aza-1,4-dioxa-8-phenylspiro[4,5]decan-2-yl)methyl 3-oxobutanoate A mixture of 19 g ($7.66 \cdot 10^{-2}$ mol) of (8-aza-1,4-dioxa-8-phenylspiro[4,5]decan-2-yl)methanol, 14.2 g ($7.66 \cdot 10^{-2}$ mol) of acetylated Meldrum's acid (compound of the formula V) and 200 ml of toluene is heated under reflux for 3 hours. The solvent is evaporated off and the crude product obtained is purified by flash chromatography, elution being carried out with a toluene/ethyl acetate mixture (19:1 v/v) and then a hexane/acetone mixture (19:1 v/v). This gives 19.8 g (yield: 78%) of the expected product in the form of a yellow oil.

NMR spectrum: 80 MHz TMS (CDCl$_3$) 1.7–2 (4H, m); 2.26 (3H, s); 3.2–2.45 (4H, m); 3.5 (2H, s); 3.6–4.5 (5H, m); 6.7–7.3 (5H, m).

PREPARATION II

Preparation of (8-aza-1,4-dioxa-8-phenylspiro[4,5]decan-2-yl)methyl aminocrotonate 19.8 g ($5.96 \cdot 10^{-2}$ mol) of the product obtained in Preparation I are dissolved in 200 ml of methanol. Ammonia gas dried over potassium hydroxide is bubbled for 2 hours into the solution kept at 0° C. and then for 4 hours at room temperature. The solvent is evaporated off and the crude product obtained is purified by flash chromatography, elution being carried out with a hexane/acetone mixture (19:1 v/v) and then a hexane/acetone mixture (9:1 v/v). This gives 15 g (yield: 75%) of the expected product in the form of a pale yellow oil.

NMR spectrum: 80 MHz TMS (CDCl$_3$) 1.7–2 (m) and 1.89 (s) (7H); 3.2–3.45 (4H, m); 2.5–4.5 (5H, m); 4.55 (1H, s); 6.7–7 (3H, m); 7.2–7.3 (2H, m).

PREPARATION III

Preparation of methyl (8-aza-1,4-dioxa-8-phenylspiro[4,5]decan-2-yl)methyl 1,4-dihydro-2,6-dimethyl-4-(3-nitrophenyl)pyridine-3,5-dicarboxylate

Example 2

A mixture of 14.7 g ($4.44 \cdot 10^{-2}$ mol) of the product obtained in Preparation II and 11 g ($4.44 \cdot 10^{-2}$ mol) of methyl 3-nitrobenzylideneacetylacetate in 300ml of tertiary butanol is heated under reflux for 4 hours. The solvent is evaporated off and the crude product is purified by flash chromatography, elution being carried out with a hexane/acetone mixture (19:1 v/v), then a toluene/isopropanol mixture (100:1 v/v) and then a hexane/acetone mixture (8:2 v/v). This gives 5.7 g (yield: 25%) of a yellow oil, which solidifies in the form of an amorphous foam melting at 89° C.

NMR spectrum: 80 MHz TMS (CDCl$_3$) 1.8 (4H, m); 2.36 (6H, s); 3.3 (4H, m); 3.5–4.3 (8H, m); 5.11 (1H, s); 5.8 (1H, s); 6.8–8.1 (9H, m).

PREPARATION IV

Preparation of methyl (8-aza-1,4-dioxa-8-phenylspiro[4,5]decan-2-yl)methyl 1,4-dihydro-2,6-dimethyl-4-(3-nitrophenyl)pyridine-3,5-dicarboxylate

Example 2

2.03 g ($0.5 \cdot 10^{-2}$ mol) of methyl 1,2-dihydroxypropan-3-yl 1,4-dihydro-2,6-dimethyl-4-(3-nitrophenyl)pyridine-3,5-dicarboxylate are dissolved in 10 ml of methanol, and 0.96 g ($0.55 \cdot 10^{-2}$ mol) of N-phenylpiperidin-4-one, 20 ml of toluene and 0.3 g of paratoluenesulfonic acid are then added. The mixture is heated for 3 hours under reflux and then brought back to room temperature and hydrolyzed in 100 ml of a saturated aqueous solution of sodium bicarbonate. The reaction medium is then extracted three times with 30 ml portions of ethyl acetate. The organic phases obtained are combined and washed three times with 20 ml portions of water. The organic solution obtained is dried over magnesium sulfate and filtered and the solvent is evaporated off. The oil obtained is purified by flash chromatography, elution being carried out with a toluene/isopropanol mixture (95:5 v/v). This gives 15.5 g (yield: 55%) of the expected product in the form of a yellow foam with characteristics identical to those of the product obtained in Preparation III.

PREPARATION V

Preparation of methyl (8-aza-8-(4-chlorophenyl)-1,4-dioxaspiro[4.5]decan-2-yl)methyl 1,4-dihydro-2,6-dimethyl-4-(3-nitrophenyl)pyridine-3,5-dicarboxylate

Example 11

2.03 g ($0.5 \cdot 10^{-2}$ mol) of methyl 1,2-dihydroxypropan-3-yl 1,4-dihydro-2,6-dimethyl-4-(3-nitrophenyl)-pyridine-3,5-dicarboxylate are dissolved in 10 ml of methanol, and 1.15 g ($0.55 \cdot 10^{-2}$ mol) of N-(4-chlorophenyl)piperidin-4-one, 20 ml of toluene and 0.2 g of paratoluenesulfonic acid are then added. The mixture is heated for 3 hours under reflux and then cooled to room temperature and hydrolyzed in 100 ml of a saturated aqueous solution of sodium bicarbonate. The reaction medium is extracted three times with 30 ml portions of ethyl acetate. The organic phases are combined and washed three times with 20 ml portions of water and then dried over magnesium sulfate and filtered and the solvent is evaporated off. The oil obtained is purified by flash chromatography, elution being carried out with a toluene/isopropanol mixture (95:5 v/v). This gives 1.7 g (yield: 57%) of the expected product in the form of a crystalline powder which melts at 145°-150° C.

NMR spectrum: 80 MHz TMS (CDCl$_3$) 1.8 (4H, m); 2.36-2.38 (6H, 2s); 3.26 (4H, m); 3.5-4.4 (m) including 3.64 (s) and 3.65 (s) (8H); 5.12 (1H, s); 5.85 (1H, s); 6.6-8.1 (8H, m).

PREPARATION VI

Preparation of (8-aza-8-(4-chlorophenyl)-1,4-dioxaspiro[4,5]decan-2-yl)methyl 3-oxobutanoate A mixture of 3.5 g (0.0122 mol) of (8-aza-8-(4-chlorophenyl)-1,4-dioxaspiro[4,5]decan-2-yl)methanol, 2.95 g (0.0159 mol) of acetylated Meldrum's acid and 100 ml of toluene is heated under reflux for one hour. The solvent is then evaporated off and the oil obtained is purified by flash chromatography, elution being carried out with a toluene/ethyl acetate mixture (8:2 v/v). This gives 3.5 g (yield: 78%) of a yellow solid melting at 59° C.

NMR spectrum: 80 MHz TMS (CDCl$_3$) 1.65-2 (4H, m); 2.27 (3H, s); 3.1-3.4 (4H, m); 3.5 (2H, s); 3.6-4.5 (5H, m); 6.83 (2H, d); 7.2 (2H, d).

PREPARATION VII

Preparation of (8-aza-8-(4-chlorophenyl)-1,4-dioxaspiro[4,5]decan-2-yl)methyl aminocrotonate Ammonia gas dried over potassium hydroxide is bubbled into a mixture of 3.5 g ($0.95 \cdot 10^{-2}$ mol) of (8-aza-8-(4-chlorophenyl)-1,4-dioxaspiro[4,5]decan-2-yl)methyl 3-oxobutanoate, 100 ml of dry methylene chloride and 5 g of a 4 Å molecular sieve at room temperature for 6 h and the reaction medium is then stirred for 12 hours. The molecular sieve is filtered off and the solvent is evaporated off. This gives 3.06 g of a crystalline yellow product melting at 60° C. (yield: 88%).

NMR spectrum: 80 MHz TMS (CDCl$_3$) 1.7-2 (m) and 1.91 (s) (7H); 3.1-3.4 (4H, m); 3.6-4.5 (5H, m); 4.56 (1H, s); 6.75-6.90 (2H, d); 7.1-7.25 (2H, d).

PREPARATION VIII

Preparation of methyl (8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate

Example 11

A mixture of 3.1 g ($0.85 \cdot 10^{-2}$ mol) of (8-aza-8-(4-chlorophenyl)-1,4-dioxaspiro[4,5]decan-2-yl)methyl aminocrotonate, 2.1 g ($0.85 \cdot 10^{-2}$ mol) of methyl 3-nitrobenzylideneacetylacetate and 100 ml of tertiary butanol is heated under reflux for eight hours. The solvent is evaporated off and the crude product obtained is purified by flash chromatography, elution being carried out with a toluene/isopropanol mixture (95:5 v/v) and then a hexane/acetone mixture (8:2 v/v). This gives 1.7 g (yield: 35%) of the expected product with physical characteristics identical to those of the product obtained in Preparation V.

PREPARATION IX

Preparation of methyl (8-aza-1,4-dioxa-8-phenylspiro[4,5]decan-2-yl)methyl 1,4-dihydro-2,6-dimethyl-4-(3-nitrophenyl)pyridine-3,5-dicarboxylate

Example 12

A mixture of 0.22 g ($5 \cdot 10^{-4}$ mol) of methyl (2,2-dimethyl-1,3-dioxolan-4-yl)methyl 1,4-dihydro-2,6-dimethyl-4-(3-nitrophenyl)pyridine-3,5-dicarboxylate, 0.26 g ($1.5 \cdot 10^{-5}$ mol) of N-phenylpiperidin-4-one, 8 ml of toluene and 35 mg of paratoluenesulfonic acid is heated under reflux for 6 h. The reaction mixture is hydrolyzed in a saturated aqueous solution of sodium bicarbonate. The medium obtained is extracted with ethyl acetate. The organic phases obtained are washed with water, dried over magnesium sulfate and filtered and the solvent is evaporated off. The crude product obtained is purified by flash chromatography, elution being carried out with a toluene/isopropanol mixture (98:2 v/v). This gives 0.07 g (yield: 25%) of the expected product with physical characteristics identical to those of the product obtained in Preparation III.

PREPARATION X

Preparation of methyl (8-aza-1,4-dioxa-8-(4-hydroxyphenyl)spiro[4,5]decan-2-yl)methyl 1,4-dihydro-2,6-dimethyl-4-(3-nitrophenyl)pyridine-3,5-dicarboxylate

Example 14

If the procedure described in Preparation IV is followed and a mixture of 6 g (0.015 mol) of methyl 1,2-dihydroxypropan-3-yl 1,4-dihydro-2,6-dimethyl-4-(3-nitrophenyl)pyridine-3,5-dicarboxylate, 1.9 g (0.01 mol) of N-(4-hydroxyphenyl)piperidin-4-one and 0.5 g of paratoluenesulfonic acid in 30 ml of butanol and 60 ml of toluene is heated under reflux for 11 h, 2.2 g (yield: 38%) of the expected product are obtained in the form of a foam after two successive purifications by flash chromatography, elution being carried out with a hexane/acetone mixture (1:1 v/v).

M.p. = 102° to 114° C.

NMR spectrum: 80 MHz TMS (CDCl$_3$) 1.7-2 (4H, m); 2.37 (6H, s); 3.0-3.3 (4H, m); 3.63 and 3.64 (3H, ds); 3.6-4.5 (5H, m); 5.12 (1H, s); 6.08 (1H, s); 6.70 and 6.88 (4H, dd); 7.25-8.15 (4H, m).

PREPARATION XI

Preparation of methyl (8-aza-1,4-dioxa-8-(4-methylphenyl)spiro[4,5]decan-2-yl)methyl 1,4-dihydro-2,6-dimethyl-4-(3-nitrophenyl)pyridine-3,5-dicarboxylate

Example 15

If the procedure described in Prepration IV is followed and a mixture of 2 g (0.005 mol) of methyl 1,2-dihydroxypropan-3-yl 1,4-dihydro-2,6-dimethyl-4-(3-nitrophenyl)pyridine-3,5-dicarboxylate, 1.86 g (0.01 mol) of N-(4-methylphenyl)piperidin-4-one and 0.2 g of paratoluenesulfonic acid in 20 ml of toluene and 10 ml of butanol is heated under reflux for 24 hours, 2.1 g (yield: 70%) of the expected product, melting over the range from 75° to 85° C., are obtained in the form of a foam after two successive purifications by flash chromatography, elution being carried out with a hexane-/acetone mixture (6:4 v/v) and then ether.

NMR spectrum: 80 MHz TMS (CDCl$_3$) 1.7–1.95 (4H, m); 2.26 (3H, s); 2.35 (6H, s); 3.05–3.3 (4H, m); 3.63 (3H, s); 3.6–4.5 (5H, m); 5.12 (1H, s); 6.17 (1H, s); 6.8 and 7.07 (4H, dd); 7.2–8.15 (4H, m).

PREPARATION XII

Preparation of (8-aza-1,4-dioxa-8-(4-trifluoromethylphenyl)-spiro[4,5]decan-2-yl)methyl 3-oxobutanoate A mixture of 4.75 g (0.015 mol) of (8-aza-1,4-dioxa-8-(4-trifluoromethylphenyl)spiro[4,5]decan-2-yl)methanol, 3 g (0.016 mol) of acetylated Meldrum's acid (compound of the formula V) and 50 ml of toluene is heated under reflux for two hours. The mixture is brought back to room temperature and water is added. The organic phase is decanted and then washed with water until the pH of the washings is neutral, and dried. This gives 6 g of an oil.

NMR spectrum: 80 MHz TMS (CDCl$_3$) 1.5–2 (4H, m); 2.27 (3H, 2); 3.3–4.6 (m)+3.5 (s) (6H); 4–4.5 (5H, m); 6.8–6.95 (2H, d); 7.35–7.5 (2H, d).

PREPARATION XIII

Preparation of (8-aza-1,4-dioxa-8-(4-trifluoromethylphenyl)-spiro[4,5]decan-2-yl)methyl aminocrotonate 6 g (0.015 mol) of the product obtained in Preparation XII are dissolved in 100 ml of chloroform. Ammonia gas is bubbled into the solution for 3 hours and then for a further 8 hours after a molecular sieve has been added to the reaction medium. The mixture is filtered and the organic phase obtained is evaporated. This gives 6 g of a solid melting at 122° C.

NMR spectrum: 80 MHz TMS (CDCl$_3$) 1.7–2 (m)+1.9 (s) (7H); 3.25–3.6 (4H, m); 3.7–4.4 (5H, m); 4.56 (1H, s); 6.8–6.95 (2H, d); 7.35–7.5 (2H, d).

PREPARATION XIV

Preparation of methyl (8-aza-1,4-dioxa-8-(4-trifluoromethylphenyl)-spiro[4,5]decan-2-yl)methyl 1,4-dihydro-2,6-dimethyl-4-(3-nitrophenyl)pyridine-3,5-dicarboxylate A mixture of 6 g (0.015 mol) of the product obtained in Preparation XIII and 3.7 g (0.015 mol) of methyl 3-nitrobenzylideneacetylacetate in tertiary butanol is heated under reflux for 1 hour. The solvent is evaporated off and the crude product is successively purified twice by flash chromatography, elution being carried out with a toluene/isopropanol mixture (9:1 v/v) and then a toluene/isopropanol mixture (19:1 v/v). This gives 2.3 g (yield: 25%) of an oil, which solidifies in the form of an amorphous foam melting over the range from 65° to 95° C.

NMR spectrum: 80 MHz TMS (CDCl$_3$) 1.8 (4H, m); 2.36–2.38 (6H, ds); 3.4 (4H, m); 3.5–4.5 (m)+3.64 (s)+3.65 (s) (8H); 5.12 (1H, s); 5.76 (1H, s); 6.7–8.1 (8H, m).

PREPARATION XV

Preparation of methyl (8-aza-8-(2,4-dichlorophenyl)-1,4-dioxaspiro[4,5]decan-2-yl)methyl 1,4-dihydro-2,6-dimethyl-4-(3-nitrophenyl)pyridine-3,5-dicarboxylate

Example 16

If the procedure described in Preparation IV is followed starting from 4.06 g (10$^{-2}$ mol) of methyl 1,2-dihydroxypropan-3-yl 1,4-dihydro-2,6-dimethyl-4-(3-nitrophenyl)pyridine-3,5-dicarboxylate and 2.44 g (10$^{-2}$ mol) of N-(2,4-dichlorophenyl)piperidin-4-one, 5.6 g (yield: 90%) of the expected product are obtained, which melts over the range from 80° to 95° C.

NMR spectrum: 80 MHz TMS (CDCl$_3$) 1.87 (4H, m); 2.39 (6H, s); 3.05 (4H, m); 3.5–4.4 (m) and 3.64 (s) (8H); 5.12 (1H, s); 5.99 (1H, s); 6.95–8.1 (7H, m).

PREPARATION XVI

Preparation of methyl 1,2-dihydroxypropan-3-yl 1,4-dihydro-2,6-dimethyl-4-(3-nitrophenyl)pyridine-3,5-dicarboxylate (intermediate involved in Preparation IV above)

11.1 g (2.48·10$^{-2}$ mol) of methyl (2,2-dimethyl-1,3-dioxolan-4-yl)methyl 1,4-dihydro-2,6-dimethyl-4-(3-nitrophenyl)pyridine-3,5-dicarboxylate, 50 ml of methanol and 50 ml of 1N HCl are introduced into a 250 ml round-bottomed flask. The reaction medium is stirred for 1 h at 15°–20° C. and then neutralized with NaHCO$_3$. The methanol is evaporated off and the residue is extracted with 100 ml of ethyl acetate. The ethyl acetate phase is washed with water until the pH of the washings is neutral, and then dried (over MgSO$_4$) and filtered and the filtrate is evaporated under reduced pressure. The evaporation residue is collected (9.2 g; yield: 91%); this product is in the form of a yellow foam melting at 90° C. and essentially consists of methyl 1,2-dihydroxypropan-3-yl 1,4-dihydro-2,6-dimethyl-4-(3-nitrophenyl)pyridine-3,5-dicarboxylate.

NMR spectrum: 80 MHz TMS (CDCl$_3$) 1.73 (1H, s); 2.37 (7H, s); 3.5 (2H, m); 3.6 (3H, s); 3.8 (1H, m); 4.19 (2H, m); 5.1 (1H, s); 6.01 (1H, s); 7.3–8.03 (4H, m).

PREPARATION XVII

Preparation of (R)-8-aza-1,4-dioxa-8-(4-chlorophenyl)-2-(2-propenyloxymethyl)spiro[4,5]decane A mixture of 16 g (0.075 mol) of N-(4-chlorophenyl)-piperidin-4-one, 1.6 g of paratoluenesulfonic acid and 70 ml of anhydrous methanol is heated under reflux. When the ketal has been formed, 10 g (0.075 mol) of (S)-3-(2-propenyloxy)propane-1,2-diol are added. The methanol is then distilled and replaced with toluene. After a reaction time of one hour, the reaction mixture is left to cool to room temperature. It is hydrolyzed in a saturated aqueous solution of sodium bicarbonate. The medium obtained is extracted with ethyl acetate. The organic phases are washed with water, dried over magnesium sulfate and filtered and the solvent is evaporated off. The crude product obtained is purified by flash chromatography, elution being carried out with a hexane/acetone mixture (9:1 v/v). This gives 16 g (yield: 75%) of the pure product with the following physical characteristics:

NMR spectrum: 80 MHz TMS (CDCl$_3$) 1.7-2 (4H, m); 3.1-3.4 (4H, m); 3.5-4.5 (7H, m); 5.05-5.45 (2H, m); 5.75-6.2 (1H, m); 6.83 (2H, d); 7.2 (2H, d)

Optical rotation: C=0.65 g/100 ml (methanol) [α]$_D^{20}$=−8.2

Melting point: 40° C.

PREPARATION XVIII

Preparation of (S)-8-aza-1,4-dioxa-8-(4-chlorophenyl)-2-(2-propenyloxymethyl)spiro[4,5]decane If a procedure analogous to the previous preparation is followed and (R)-3-(2-propenyloxy)propane-1,2-diol is reacted with the ketal, the expected product is obtained, its NMR spectrum and melting point being identical to those of the product obtained in the previous preparation.

Optical rotation: C=0.65 g/100 ml (methanol) [α]$_D^{20}$=+10.3.

PREPARATION XIX

Preparation of (R)-8-aza-2-hydroxymethyl-1,4-dioxa-8-(4-chlorophenyl)spiro[4,5]decane 20.1 g (0.062 mol) of the product obtained in Preparation XVII are dissolved in a mixture of 450 ml of acetone and 45 ml of water. A mixture of 15.7 g of mercuric oxide and 18.5 g of mercuric chloride in 110 ml of an acetone/water mixture (10:1 v/v) is added dropwise at room temperature. The reaction medium is stirred for one hour and then filtered on Celite ® and the solvent is evaporated off. The residue is subsequently taken up in ether and then washed with an aqueous solution of potassium iodide. The ether is evaporated off. The crude product obtained is purified by flash chromatography, elution being carried out with a toluene/ethyl acetate mixture (8:2 v/v). This gives 16.3 g (yield: 93%) of the expected product in the form of white crystals.

Optical rotation: C=0.46 g/100 ml (methanol) [α]$_D^{20}$=−4.0

Melting point: 125° C.

PREPARATION XX

Preparation of (S)-8-aza-2-hydroxymethyl-1,4-dioxa-8-(4-chlorophenyl)spiro[4,5]decane If a procedure analogous to the previous preparation is followed starting from the product obtained in Preparation XVIII, the expected product is obtained with the following physical characteristics:

Optical rotation: C=0.46 g/100 ml (methanol) [α]$_D^{20}$=+4.9

Melting point: 130° C.

PREPARATION XXI

Preparation of methyl (8-aza-8-(4-chlorophenyl)-1,4-dioxaspiro[4,5]decan-2-yl)methyl N-(ethoxymethyl)-1,4-dihydro-2,6-dimethyl-4-(3-nitrophenyl)pyridine-3,5-dicarboxylate (R-(R*,S*))

2.925 g (0.0075 mol) of (R)-N-(Ethoxymethyl)-1,4-dihydro-2,6-dimethyl-4-(3-nitrophenyl)-3-methoxycarboxylpyridine-5-carboxylic acid and 1.34 g (0.0082 mol) of carbonyldiimidazole are dissolved in 50 ml of dimethylformamide. The mixture is heated at 40° C. for one hour. 2.13 g (0.0075 mol) of the product obtained in Preparation XX and 1.12 ml (0.0075 mol) of 1,8-diazabicyclo[5.4.0]undec-7-ene are then added to the reaction medium. The mixture is heated to 100° C. After 2 hours, the mixture is left to cool and then poured into 100 ml of water. The medium is extracted 3 times with 30 ml of ethyl acetate. The organic phases obtained are washed twice with 10 ml of water, dried over magnesium sulfate and filtered and the solvent is evaporated off. The crude product obtained is purified by flash chromatography, elution being carried out with a toluene/isopropanol mixture (97:3 v/v). This gives 4.8 g (yield: 98%) of an oil.

NMR spectrum: 80 MHz TMS (CDCl$_3$) 1.23 (3H, t); 1.65-2 (4H, m); 2.56 (6H, s); 3.05-3.35 (4H, m); 3.47 (2H, q); 3.69 (3H, s, s); 3.50-4.40 (5H, m); 4.86 (2H, s); 5.19 (1H, s); 6.83 (2H, d); 7.19 (2H, d); 7.25-7.75 (2H, m); 7.8-8.1 (2H, m).

PREPARATION XXII

Preparation of methyl (8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate (R-(R*,S*))

Example 17

4.9 g (0.0075 mol) of the product obtained in Preparation XXI are dissolved in 120 ml of acetone, 25 ml of N hydrochloric acid and 10 ml of water. The mixture is stirred at room temperature for 8 hours. The reaction medium is poured into 200 ml of an aqueous solution of sodium bicarbonate. Extraction is carried out 3 times with 50 ml of ethyl acetate. The organic phases are washed twice with 20 ml of water and dried over magnesium sulfate and the solvent is evaporated off. The crude product obtained is purified on a chromatography column, elution being carried out with ether. This gives 3 g (yield: 67%) of the expected product melting at 171° C.

NMR spectrum: 500 MHz TMS (CDCl$_3$) 1.82 (4H, m); 2.38 (6H, d); 3.26 (4H, m); 3.66 (3H, s); 3.73 (1H, m); 4.05 (1H, m); 4.10 (2H, m); 4.32 (1H, m); 5.11 (1H, s); 5.87 (1H, s); 6.85 (2H, m); 7.19 (2H, m); 7.37 (1H, m); 7.66 (1H, m); 8.00 (1H, m); 8.10 (1H, m)

Optical rotation: C=0.5 g/100 ml (methanol) [α]$_D^{20}$=+29.2.

PREPARATION XXIII

Preparation of methyl (8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate (S-(R*,R*))

Example 18

If a procedure analogous to Preparations XXI and XXII is followed starting from (R)-N-(ethoxymethyl)-1,4-dihydro-2,6-dimethyl-4-(3-nitrophenyl)-3-methoxycarbonylpyridine-5-carboxylic acid and the product obtained in Preparation XIX, the expected product is obtained, which melts at 175° C.

NMR spectrum: 500 MHz TMS (CDCl$_3$) 1.80 (4H, m); 2.37 (6H, d); 3.25 (4H, m); 3.85 (1H, m); 3.64 (3H, s); 3.97 (1H, m); 4.10 (2H, m); 4.33 (1H, m); 5.10 (1H, s); 5.83 (1H, s); 6.85 (2H, d); 7.20 (2H, d); 7.38 (1H, m); 7.65 (1H, m); 8.00 (1H, m); 8.10 (1H, m) Optical rotation: C=0.46 g/100 ml (methanol) [α]$_D^{20}$=+14.6.

PREPARATION XXIV

Preparation of methyl (8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate (S-(R*,S*))

Example 19

If a procedure analogous to Preparations XXI and XXII is followed starting from (S)-N-(ethoxymethyl)-1,4-dihydro-2,6-dimethyl-4-(3-nitrophenyl)-3-methoxycarbonylpyridine-5-carboxylic acid and the product obtained in Preparation XIX, the expected product is obtained, which melts at 151°–154° C.

NMR spectrum: 500 MHz TMS (CDCl$_3$) 1.81 (4H, m); 2.38 (6H, d); 3.26 (4H, m); 3.66 (3H, s); 3.73 (1H, m); 4.05 (1H, m); 4.10 (1H, m); 4.32 (1H, m); 5.11 (1H, s); 5.86 (1H, s); 6.84 (2H, m); 7.19 (2H, m); 7.37 (1H, m); 7.66 (1H, m); 7.99 (1H, m); 8.10 (1H, m) Optical rotation: C=0.5 g/100 ml (methanol) $[\alpha]_D^{20}$ = −23.0.

PREPARATION XXV

Preparation of methyl (8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate (R-(R*,R*))

Example 20

If a procedure analogous to Preparations XXI and XXII is followed starting from (S)-N-(ethoxymethyl)-1,4-dihydro-2,6-dimethyl-4-(3-nitrophenyl)-3-methoxycarbonylpyridine-5-carboxylic acid and the product obtained in Preparation XX, the expected product is obtained, which melts at 176°–179° C.

NMR spectrum: 500 MHz TMS (CDCl$_3$) 1.80 (4H, m); 2.37 (6H, d); 3.25 (4H, m); 3.59 (1H, m); 3.65 (3H, s); 3.97 (1H, m); 4.12 (2H, m); 4.33 (1H, m); 5.10 (1H, s); 5.87 (1H, s); 6.84 (2H, m); 7.17 (2H, m); 7.38 (1H, m); 8.00 (1H, m); 8.10 (1H, m)

Optical rotation: C=0.4 g/100 ml (methanol) $[\alpha]_D^{20}$ = −10.9.

PREPARATION XXVI

Preparation of methyl (8-aza-8-(4-chlorophenyl)-1,4-dioxaspiro[4,5]decan-2-yl)methyl 1,4-dihydro-2,6-dimethyl-4-(2,3-dichlorophenyl)pyridine-3,5-dicarboxylate

Example 21

If the procedure described in Preparation VIII is followed and a mixture of 2.73 g (0.01 mol) of methyl 2,3-dichlorobenzylideneacetylacetate, 3.66 g (0.01 mol) of (8-aza-8-(4-chlorophenyl)-1,4-dioxaspiro[4,5]decan-2-yl)methyl aminocrotonate and 30 ml of t.butanol is heated under reflux for one hour, 2.6 g (yield: 42%) of the expected product melting at 100° C. are obtained after a first purification by flash chromatography, elution being carried out with an ether/hexane mixture (1:1 v/v) and then a second purification by flash chromatography, elution being carried out with ether, and after recrystallization from ethanol.

NMR spectrum: 80 MHz TMS (CDCl$_3$) 1.77 (4H, m); 2.31 (6H, d); 3.25 (4H, m); 3.40–4.40 (5H, m); 3.60 (3H, s); 5.44 (1H, s); 5.74 (1H, s); 6.80 (2H, d); 7.13 (2H, d); 7.00–7.40 (3H, m).

A number of products obtained by the procedure described in Preparation III have been collated in Table IV below. The solvent used is tertiary butanol and the reaction temperature is the reflux temperature of the reaction medium. The table indicates the weight of the reactants, the reaction time, the method of purification used, the resulting weight of the product of the formula I according to the invention, the yield of the reaction and also the NMR spectrum of the expected product.

TABLE IV

| Ex. | Aminocrotonate III (g) | Nitrobenzylidene-acetoacetate II (g) | Time (hours) | Method of purification | Weight obtained (g) | Yield (%) | NMR spectrum |
|---|---|---|---|---|---|---|---|
| 1 | 2.5 | 1.8 | 2.5 | 4 × flash chromatography toluene/ethyl acetate (8:7 v/v) toluene/isopropanol (19:1 v/v) toluene/isopropanol (9:1 v/v) toluene/ethyl acetate/ triethylamine (80:5:5 v/v/v) | 2.1 | 50 | 1.7 (4H, m); 2.5 (m) + 2.36 (s) (10 H); 3–4.3 (m) + 3.6 (s) + 3.5 (s) (10 H); 5.1 (1H, s); 6.0 (1H, s); 7.2–8.08 (9H, m) |
| 3 | 5.2 | 4.8 | 4 | 2 × flash chromatography chloroform/methanol (50:1 v/v) toluene/isopropanol/ triethylamine (190:10:1 v/v/v) | 3.9 | 40 | 1.76 (4H, m); 2.49 (m) + 2.34 (s) + 2.3 (s) (13H); 3.65 (3H, s); 3.5–4.4 (5H, m); 5.11 (1H, s); 6.06 (1H, s); 7.2–8.08 (4H, m) |
| 4 | 6.4 | 4.4 | 1 | flash chromatography hexane/acetone (7:3 v/v) | 6 | 56 | 1.83 (4H, m); 2.36 (6H, s); 3.16 (4H, m); 3.63 (3H, s); 3.64 (3H, s); 3.7 (3H, s); 3.5–4.4 (5H, m); 5.12 (1H, s); 5.89 (1H, s); 6.7–8.1 (8H, m) |
| 5 | 7 | 4.4 | 1 | flash chromatography hexane/acetone (7:3 v/v) | 2.5 | 22 | 1.85 (4H, m); 2.36 and 2.38 (6H, ds); 3.17 (4H, m); 3.5–4.4 (m) + 3.64 (s) + 3.83 (s) + 3.87 (s) (14H); 5.12 (1H, s); 5.85 (1H, s); 6.4– |

TABLE IV-continued

| Ex. | Aminocrotonate III (g) | Nitrobenzylidene-acetoacetate II (g) | Time (hours) | Method of purification | Weight obtained (g) | Yield (%) | NMR spectrum |
|---|---|---|---|---|---|---|---|
| 6 | 9 | 6.5 | 1 | 2 × flash chromatography hexane/acetone (7:3 v/v) ether | 2.5 | 18 | 8.1 (7H, m) 1.8 (4H, m); 2.36 and 2.38 (6H, ds); 3.2 (4H, m); 3.5–4.5 (m) + 3.60 and 3.65 (ds) (8H); 5.11 (1H s); 5.9 (1H, s); 6.8–8.1 (8H, m) |
| 7 | 15.4 | 10.5 | 12 | 3 × flash chromatography hexane/acetone (7:3 v/v) toluene/isopropanol (20:1 v/v) hexane/acetone (6:4 v/v) | 3.3 | 13 | 1.66 (4H, m); 2.33 and 2.35 (6H, ds); 3.5–4.2 (m) + 3.6 (s) (12H); 5.1 (1H, s); 6.2 (1H, s); 7.3–8.1 (9H, m) |
| 8 | 10.46 | 7.2 | 10 | 4 × flash chromatography toluene/isopropanol (98:2 v/v) toluene/isopropanol (97:3 v/v) toluene/isopropanol (97:3 v/v) ether/acetone (1:1 v/v) | 3.7 | 22 | 1.9 (4H, m); 2.37 and 2.39 (6H, ds); 3.28 (4H, m); 3.5–4.5 (m) + 3.64 (ds) (8H); 5.19 (1H, s); 5.95 (1H, s); 7–8.1 (8H, m) |
| 9 | 6 | 3.96 | 4 | 3 × flash chromatography toluene/isopropanol (98:2 v/v) toluene/isopropanol (98:2 v/v) ether/acetone (1:1 v/v) | 4.1 | 42 | 1.78 (4H, m); 2.36 and 2.39 (6H, ds); 3.2–4.2 (12H, m); 5.12 (1H, s) 6.07 (1H, s); 6.6–8.14 (8H, m) |
| 10 | 3.1 | 2.5 | 3 | 2 × flash chromatography toluene/isopropanol (98:2 v/v) ether | 3.1 | 60 | 1.77 (4H, m); 2.36 and 2.38 (6H, ds); 3.2–4.4 (m); 3.64 and 3.65 (ds) (12H); 5.11 (1H, s); 6.05 (1H, s); 6.6–8.1 (8H, m) |
| 12 | 6 | 3.7 | 1 | 2 × flash chromatography toluene/isopropanol (9:1 v/v) toluene/isopropanol (9:1 v/v) | 2.3 | 25 | 1.8 (4H, m); 2.36 and 2.38 (6H, ds); 3.4 (4H, m); 3.5–4.5 (m) + 3.64 and 3.65 (ds) (8H); 5.12 (1H, s); 5.76 (1H, s); 6.7–8.1 (8H, m) |
| 13 | 4.4 | 2.5 | 1 | 2 × flash chromatography toluene/ethyl acetate (10:1 v/v) hexane/acetone (3:1 v/v) | 1.5 | 24 | 1.5–1.95 (4H, m); 2.37 (6H, s); 3.1–3.45 (m, 4H); 3.5–4.4 (m) + 3.64 (s) (8H); 5.13 (1H, s); 6.04 (1H, s); 7–8.15 (8H, m) |

The antihypertensive activity of the products according to the invention was demonstrated by oral administration to spontaneously hypertensive rats aged between 16 and 20 weeks. The systolic arterial pressure is measured by plethysmography and the heart rate is obtained from the pressure trace. The compounds studied are administered orally. The maximum antihypertensive effects obtained are collated in Table V below. Unless indicated otherwise, groups of 6 animals were used. The statistical significance of the effect after 24 hours is given in brackets, where * denotes $p<0.05$,  denotes $p<0.01$ and * denotes $p<0.001$ according to a variance analysis followed by a Student t test.

The products according to the invention, and nicardipine taken as the reference, were also tested by oral administration to perinephritic hypertensive dogs. Mongrel dogs weighing 20 to 25 kg or beagle dogs weighing 10 to 15 kg are rendered hypertensive by enclosing both kidneys in a sheet of cellophane in accordance with the technique described by I. H. Page (J.A.M.A., vol. 113, no. 23, pp 2046-48, 1939). Ten to twelve weeks after the intervention and after the animals have been conditioned for measurements, the systolic arterial pressure and the heart rate are measured using a piezoelectric sensor and an inflatable sleeve (Apelex-BP recorder). The products are administered orally at a dose of 3 mg/kg and the parameters are measured 0.5, 1, 2, 4, 6, 8 and 24 hours after administration.

By way of example, a drop in the systolic arterial pressure of $(44.3\pm4.8)$ % was observed for the compound of Example 11, the effect lasting more than 24 hours. Nicardipine causes a drop in systolic arterial pressure of $(25.8\pm17.6)$ %, the effect lasting no longer than 6 hours.

TABLE V

| | Antihypertensive activity in spontaneously hypertensive rats (oral administration) | | |
|---|---|---|---|
| Product | Dose (mg/kg) | % Variation in the systolic pressure ± standard deviation | Duration of the effect |
| Ex. 1 | 30 | −54.1 ± 5.2 | 8 to 24 |

TABLE V-continued

Antihypertensive activity in spontaneously hypertensive rats (oral administration)

| Product | Dose (mg/kg) | % Variation in the systolic pressure ± standard deviation | Duration of the effect |
|---|---|---|---|
| Ex. 2 | 10 | −44.3 ± 14.8 | >24 (*) |
| Ex. 2 | 30 | −51.7 ± 5.8 | >24 (***) |
| Ex. 3 | 30 | −36.4 ± 13.3 | 8 to 24 |
| Ex. 4 | 30 | −37 ± 5 | >24 (***) |
| Ex. 5 | 30 | −43.6 ± 6.1 | >24 (*) |
| Ex. 6 | 1 (a) | −19.1 ± 10.4 | 8 to 24 |
| Ex. 6 | 3 | −29.5 ± 8.0 | 8 to 24 |
| Ex. 6 | 10 (b) | −50.1 ± 3.4 | >24 (***) |
| Ex. 6 | 30 | −52.6 ± 6.4 | >24 (***) |
| Ex. 7 | 30 | −43.7 ± 6.6 | >24 (*) |
| Ex. 8 | 30 | −19.7 ± 10.8 | >24 (*) |
| Ex. 9 | 30 | −30.8 ± 7.7 | >24 (**) |
| Ex. 10 | 30 | −36.3 ± 4.5 | 8 to 24 |
| Ex. 11 | 3 | −36.3 ± 11 | >24 (***) |
| Ex. 11 | 10 | −48.0 ± 11.1 | >24 (***) |
| Ex. 11 | 30 | −57.4 ± 6.0 | >24 (***) |
| Ex. 12 | 10 | −47.8 ± 4.6 | >24 (***) |
| Ex. 13 | 3 | −29.3 ± 9.1 | >24 (*) |
| Ex. 13 | 10 | −43.5 ± 7.0 | >24 (***) |
| Ex. 14 | 10 | −23.3 ± 12.2 | >24 (*) |
| Ex. 15 | 10 | −36.0 ± 11.3 | >24 (*) |
| Ex. 16 | 3 | −45.5 ± 7.0 | >24 (*) |
| Ex. 17 | 3 | −41.7 ± 2.7 | 8 to 24 |
| Ex. 17 | 10 | −46.8 ± 4.3 | >24 (***) |
| Ex. 18 | 3 | −29.7 ± 13.0 | 8 to 24 |
| Ex. 18 | 10 | −44.7 ± 3.1 | >24 (***) |
| Ex. 19 | 3 | −13.4 ± 7.7 | 4 |
| Ex. 19 | 10 | −32.3 ± 9.0 | 8 to 24 |
| Ex. 20 | 3 | −9.0 ± 9.6 | 6 |
| Ex. 20 | 10 | −21.3 ± 9.4 | 8 to 24 |
| Ex. 21 | 3 | −27.7 ± 10.6 | >24 (***) |
| Ex. 21 | 10 | −41.0 ± 9.3 | >24 (**) |
| nicardipine | 30 | −46.2 ± 6.8 | 8 to 24 |
| nicardipine | 10 | −43.7 ± 4.7 | 4 to 6 |

Notes:
(a): mean of 5 animals
(b): mean of 4 animals

What is claimed is:

1. An asymmetrical heterocyclic ester derivative of 1,4-dihydropyridine-3,5-dicarboxylic acid, which is selected from the group comprising:

(i) the esters corresponding to the formula:

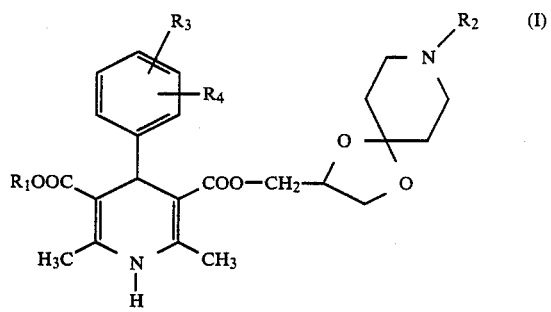

in which: $R_1$ represents a $C_1$-$C_4$ alkyl group, $R_2$ represents a $C_1$-$C_4$ alkyl group, a benzyl group, a benzoyl group or a phenyl group optionally substituted by one or more $C_1$-$C_4$ alkoxy, $C_1$-$C_4$ alkyl, cyano, nitro, hydroxyl or trifluoromethyl groups or by one or more halogen atoms, and $R_3$ and $R_4$, which are identical or different, each represent a hydrogen atom, a nitro group or a chlorine atom;

(ii) their optical isomers and diastereoisomers; and
   (iii) the corresponding addition salts.

2. A derivative according to claim 1, wherein $R_2$ is $CH_3$, $CH_2C_6H_5$, $COC_6H_5$, $C_6H_5$, 4-methoxyphenyl, 3,4-dimethoxyphenyl, 4-fluorophenyl, 2-cyanophenyl, 4-cyanophenyl, 4-nitrophenyl, 3-trifluoromethylphenyl, 4-trifluoromethylphenyl, 4-chlorophenyl, 2,4-dichlorophenyl, 4-hydroxyphenyl or 4-methylphenyl.

3. A derivative according to claim 1, wherein $R_3$ and $R_4$ form the 3-nitrophenyl group or the 2,3-dichlorophenyl group with the phenyl nucleus to which they are bonded.

4. Methyl(8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate.

5. Methyl(8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate (R-(R*,S*)).

6. Methyl(8-aza-8-(4-chlorophenyl)-1,4-dioxaspiro[4,5]decan-2-yl)methyl 1,4-dihydro-2,6-dimethyl-4-(3-nitrophenyl)pyridine-3,5-dicarboxylate (S-(R*,R*)).

7. Methyl(8-aza-8-(4-chlorophenyl)-1,4-dioxaspiro[4,5]decan-2-yl)methyl 1,4-dihydro-2,6-dimethyl-4-(2,3-dichlorophenyl)pyridine-3,5-dicarboxylate.

8. Methyl(8-aza-8-(2,4-dichlorophenyl)-1,4-dioxaspiro[4,5]decan-2-yl)methyl 1,4-dihydro-2,6-dimethyl-4-(3-nitrophenyl)pyridine-3,5-dicarboxylate.

9. A therapeutic composition which contains, in association with a physiologically acceptable excipient, at least one compound selected from the group comprising the derivatives of the formula I according to claim 1, their enantiomers and diastereoisomers and the corresponding addition salts.

10. A method of treatment of hypertension and cardiac insufficiency, which comprises administering to a human being in need of such a treatment an effective antihypertensive amount of a compound selected from the group consisting of
   (i) 1,4-dihydro-2,6-dimethylpyridine-3,5-dicarboxylic acid esters of the formula I according to claim 1;
   (ii) optical isomers and diastereoisomers thereof; and
   (iii) non-toxic addition salts thereof.

* * * * *